United States Patent
Arata et al.

(10) Patent No.: US 8,242,188 B2
(45) Date of Patent: Aug. 14, 2012

(54) DENTAL SELF-ETCHING PRIMER COMPOSITION

(75) Inventors: Masami Arata, Moriyama (JP); Akari Yamamoto, Moriyama (JP); Yoshiaki Katsura, Moriyama (JP)

(73) Assignee: Sun Medical Co., Ltd., Moriyama (JP)

( * ) Notice: Subject to any disclaimer, the term of this patent is extended or adjusted under 35 U.S.C. 154(b) by 120 days.

(21) Appl. No.: 12/447,874

(22) PCT Filed: Oct. 26, 2007

(86) PCT No.: PCT/JP2007/071355
§ 371 (c)(1),
(2), (4) Date: Apr. 29, 2009

(87) PCT Pub. No.: WO2008/053979
PCT Pub. Date: May 8, 2008

(65) Prior Publication Data
US 2010/0069527 A1 Mar. 18, 2010

(30) Foreign Application Priority Data

Oct. 30, 2006 (JP) .................................. 2006-294175

(51) Int. Cl.
*C08L 47/00* (2006.01)
(52) U.S. Cl. ........................................ 523/116; 523/118
(58) Field of Classification Search .................. 523/116, 523/118; 524/431, 493, 240; 522/47
See application file for complete search history.

(56) References Cited

U.S. PATENT DOCUMENTS

| 4,374,940 | A | * | 2/1983 | Bhatia | 523/176 |
| 5,530,038 | A | * | 6/1996 | Yamamoto et al. | 523/116 |
| 5,554,030 | A | * | 9/1996 | Ario et al. | 433/226 |
| 5,556,897 | A | * | 9/1996 | Honda et al. | 523/118 |
| 5,587,406 | A | * | 12/1996 | Yamamoto et al. | 523/116 |
| 5,670,559 | A | * | 9/1997 | Zeng et al. | 523/118 |
| 5,700,875 | A | * | 12/1997 | Zeng et al. | 525/301 |
| 5,766,328 | A | * | 6/1998 | Nakabayashi et al. | 106/35 |
| 5,834,532 | A | * | 11/1998 | Yamamoto et al. | 523/118 |
| 5,866,632 | A | * | 2/1999 | Hashimoto et al. | 523/118 |
| 6,071,983 | A | * | 6/2000 | Yamamoto et al. | 523/118 |
| 6,288,138 | B1 | * | 9/2001 | Yamamoto et al. | 523/118 |
| 6,956,033 | B2 | * | 10/2005 | Ogawa et al. | 514/230.5 |

FOREIGN PATENT DOCUMENTS

| JP | 10-251115 A | * | 9/1988 |
| JP | 06-040838 | * | 2/1994 |
| JP | 6-40838 A | | 2/1994 |
| JP | 07-082115 | * | 3/1995 |
| JP | 7-82115 A | | 3/1995 |
| JP | 07-097306 | * | 4/1995 |
| JP | 7-97306 A | | 4/1995 |
| JP | 10-251115 A | | 9/1998 |

* cited by examiner

*Primary Examiner* — James J Seidleck
*Assistant Examiner* — Peter A Salamon
(74) *Attorney, Agent, or Firm* — Birch, Stewart, Kolasch & Birch, LLP

(57) ABSTRACT

A dental self-etching primer composition and a dental self-etching primer kit comprising a mixture of (A) a polymerizable monomer, (B) a reducing inorganic compound containing sulfur, (C) a ketone-based solvent and (D) water and having a storage stability of 2 hours or longer at 65° C.

15 Claims, No Drawings

DENTAL SELF-ETCHING PRIMER COMPOSITION

TECHNICAL FIELD

The present invention relates to a dental self-etching primer composition. More specifically, it relates to a dental self-etching primer composition which is used to treat the surface of the dentine or enamel of a tooth when a composite resin is to be bonded to the dentine or enamel of the tooth by a bonding agent or when a metal or orthodontic bracket is to be bonded to the dentine or enamel of the tooth by an adhesive resin cement.

BACKGROUND ART

Along with the spread of a composite resin as a dental restoration material, strong adhesion which is easily operated, safe and reliable is required between a tooth and the composite resin. As one of conventionally used bonding methods is a typical method of bonding a restoration material in which a series of operations such as the etching of a tooth with an acid such as phosphoric acid or citric acid, rinsing in water, drying, primer treatment, drying, the application of an adhesive, polymerization and the filling of a composite resin are carried out sequentially. The bonding step in this method is complicated and takes time in the actual clinical treatment, and stable and reliable adhesion is not obtained yet.

Then, a bonding method for simplifying this complicated step is now under study. JP-A 3-240712 and JP-A 7-82115 propose a primer which eliminates an etching step. In this proposal, a tooth is treated with a self-etching primer which is said to enable etching and primer treatment to be carried out at the same time and dried, and then an adhesive is applied to the tooth. That is, the surface of the tooth having a cavity is treated with the self-etching primer to infiltrate the self-etching primer into the tooth while it melts a smear layer produced by the formation of the cavity. Then, by applying a bonding agent to the tooth, the self-etching primer and the bonding agent are cured together to obtain a strong adhesive layer.

However, currently commercially available self-etching primers of this type require a polymerization catalyst and a polymerization accelerator for curing a polymerizable component contained in the self-etching primer, and it is necessary to separate the polymerization catalyst from the polymerization accelerator in order to obtain a self-etching primer having high storage properties and stabilized adhesion performance. Therefore, currently commercially available self-etching primers are each composed of two liquid self-etching primers, i.e., one containing a polymerization catalyst and one containing a polymerization accelerator, and the two liquids must be mixed together before use. Therefore, it is hard to say that they are easy to operate, and unstable adhesion may occur due to a metering error. JP-A 6-40838 also fails to suggest the long-term storage stability of a mixed composition comprising a polymerizable component and a polymerization accelerator.

DISCLOSURE OF THE INVENTION

It is an object of the present invention to provide an adhesive primer composition which has overcome such a defect of the prior art with regard to the adhesion of a dental restoration material to a tooth that a clinically satisfactory adhesive is not obtained yet as the bonding step is complicated and takes time and stabilized adhesion strength is not obtained yet as described above and which enables a dental restoration material to be bonded to the tooth firmly and surely by a simple operation and exhibits excellent adhesion especially to the dentine.

It is another object of the present invention to provide a dental self-etching primer kit comprising the above primer composition.

Other objects and advantages of the present invention will become apparent from the following description.

According to the present invention, firstly, the above objects and advantages of the present invention are attained by a dental self-etching primer composition which comprises a mixture of (A) a polymerizable monomer, (B) a reducing inorganic compound containing sulfur, (C) a ketone-based solvent and (D) water and has a storage stability of 2 hours or longer at 65° C.

According to the present invention, secondly, the above objects and advantages of the present invention are attained by a dental self-etching primer kit comprising the dental self-etching primer composition of the present invention, wherein the kit is composed of a composition I and a composition II, and a component (E) is contained in the composition II separate from the composition I containing the component (A) and/or the component (B).

BEST MODE FOR CARRYING OUT THE INVENTION

The dental self-etching primer composition of the present invention can be directly applied to the surface of the ground tooth.

In the dental self-etching primer composition of the present invention, the component (A) is a polymerizable monomer. Examples of the polymerizable group of the monomer include radically polymerizable unsaturated groups such as acryloyl group, methacryloyl group ("(meth)acryloyl group" may be used as a generic term for the acryloyl group and the methacryloyl group hereinafter), styryl group, vinyl group and allyl group. At least one polymerizable group may be contained in one molecule. A monofunctional monomer, a bifunctional monomer and a trifunctional monomer are preferably used as polymerizable monomers containing one polymerizable group, two polymerizable groups and three polymerizable groups in one molecule, respectively. Further, these polymerizable monomers may contain a functional group such as carboxyl group, phosphoric acid group, sulfonate group, hydroxyl group, amino group or glycidyl group in the molecule.

Examples of the polymerizable monomer which can be used as the component (A) include aliphatic esters of (meth)acrylic acid such as methyl(meth)acrylate, ethyl(meth)acrylate, propyl(meth)acrylate, butyl(meth)acrylate, neopentyl glycol di(meth)acrylate and trimethylolpropane tri(meth)acrylate; (meth)acrylates containing a hydroxyl group such as 2-hydroxyethyl(meth)acrylate, 2- or 3-propyl(meth)acrylate, glycerol mono(meth)acrylate, diethylene glycol mono(meth)acrylate, triethylene glycol mono(meth)acrylate, pentaethylene glycol mono(meth)acrylate, polyethylene glycol mono(meth)acrylate, 2-hydroxy-3-phenoxypropyl(meth)acrylate and adduct of 1 mol of bisphenol A with 2 mols of glycidyl (meth)acrylate; (meth)acrylamides containing a hydroxyl group such as methylol(meth)acrylamide; polyethylene glycol di(meth)acrylates such as ethylene glycol di(meth)acrylate, diethylene glycol di(meth)acrylate, triethylene glycol di(meth)acrylate, pentaethylene glycol di(meth)acrylate, nonaethylene glycol di(meth)acrylate and tetradecaethylene glycol di(meth)acrylate; polypropylene glycol di(meth)acrylates such as propylene glycol di(meth)acrylate, dipropylene glycol di(meth)acrylate, tripropylene glycol di(meth)acrylate and nonapropylene glycol di(meth)acrylate; mono(meth)acrylates obtained by substituting the (meth)acryloyl group of either one of the above polyethylene glycol di(meth)acrylate and polypropylene glycol di(meth)acrylate by a methyl group or ethyl group; (meth)acrylates having a urethane bond such as adduct of 2-(meth)acryloyloxyethyl isocyanate, 2,2,4-trimethylhexamethylene diisocyanate or 1,3,5-trimethylhexamethylene diisocyanate with 2-hydroxyethyl(meth)acrylate; and 2,2-bis(4-(meth)acryloyloxypolyethoxyphenyl)propane obtained by condensing (meth)acrylic acid with an adduct of bisphenol A with oxyethylene. These polymerizable monomers may be used alone or in combination.

The polymerizable monomer having at least one carboxyl group in one molecule which can be used as the component (A) is selected from monocarboxylic acid, dicarboxylic acid, tricarboxylic acid, tetracarboxylic acid and derivatives thereof. Specific examples of the polymerizable monomer include (meth)acrylic acid, maleic acid, p-vinylbenzoic acid, 11-(meth)acryloyloxy-1,1-undecanedicarboxylic acid (MAC-10), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and anhydride thereof, 4-(meth)acryloyloxyethyltrimellitic acid and anhydride thereof, 4-(meth)acryloyloxybutyltrimellitic acid and anhydride thereof, 4-[2-hydroxy-3-(meth)acryloyloxy-butyl]trimellitic acid and anhydride thereof, 2,3-bis(3,4-dicarboxybenzoyloxy)propyl(meth)acrylate, N,O-di(meth)acryloyloxytyrosine, O-(meth)acryloyloxytyrosine, N-(meth)acryloyloxytyrosine, N-(meth)acryloyloxyphenylalanine, N-(meth)acryloyl-p-aminobenzoic acid, N-(meth)acryloyl-O-aminobenzoic acid, N-(meth)acryloyl-5-aminosalicylic acid, N-(meth)acryloyl-4-aminosalicylic acid, 2-, 3- or 4-(meth)acryloyloxybenzoic acid, adduct of 2-hydroxyethyl (meth)acrylate with pyromellitic dianhydride (PMDM), adduct of 2-hydroxyethyl(meth)acrylate with maleic anhydride or 3,3',4,4'-benzophenonetetracarboxylic dianhydride (BTDA) or 3,3',4,4'-biphenyltetracarboxylic dianhydride, adduct of 2-(3,4-dicarboxybenzoyloxy)-1,3-di(meth)acryloyloxypropane, N-phenylglycine or N-tolylglycine with glycidyl(meth)acrylate, 4-[(2-hydroxy-3-(meth)acryloyloxypropyl)amino]phthalic acid and 3- or 4-[N-methyl-N-(2-hydroxy-3-(meth)acryloyloxypropyl)amino]phthalic acid. Out of these, 4-(meth)acryloyloxyalkyltrimellitic acid-based compounds and acid anhydrides thereof such as 11-methacryloyloxy-1,1-undecanedicarboxylic acid (MAC-10), 4-methacryloyloxyethyltrimellitic acid (4-MET) and 4-methacryloyloxyethyltrimellitic anhydride (4-META), and N-methacryloyl-5-aminosalicylic acid (5-MASA) are preferred. Out of these, 4-methacryloyloxyethyltrimellitic acid (4-MET) is particularly preferred. A composition having excellent heat stability is obtained by containing not more than 20 wt % of 4-MET as at least part of the component (A).

These polymerizable monomers having a carboxyl group may be used alone or in combination.

Examples of the polymerizable monomer having at least one phosphoric acid group in one molecule include bis{(meth)acryloyloxyalkyl}acid phosphate-based compounds such as 2-(meth)acryloyloxyethylacid phosphate, 2- or 3-(meth)acryloyloxypropylacid phosphate, 4-(meth)acryloyloxybutylacid phosphate, 6-(meth)acryloyloxyhexylacid phosphate, 8-(meth)acryloyloxyoctylacid phosphate, 10-(meth)acryloyloxydecylacid phosphate, 12-(meth)acryloyloxydodecylacid phosphate, bis{2-(meth)acryloyloxyethyl}acid phosphate and bis{2- or 3-(meth)acryloyloxypropyl}acid phosphate; 2-(meth)acryloyloxyethylphenylacid phosphate and 2-(meth)acryloyloxyethyl-p-methoxyphenylacid phosphate. The phosphoric acid group in these compounds may be substituted by a thiophosphoric acid group. Out of these, 2-(meth)acryloyloxyethylphenylacid phosphate and 10-(meth)acryloyloxydecylacid phosphate are preferably used. These polymerizable monomers having a phosphoric acid group may be used alone or in combination.

Examples of the polymerizable monomer having at least one sulfonate group in one molecule include 2-sulfoethyl (meth)acrylate, 2- or 1-sulfo-1- or 2-propyl (meth)acrylate, 1- or 3-sulfo-2-butyl (meth)acrylate, 3-bromo-2-sulfo-2-propyl (meth)acrylate, 3-methoxy-1-sulfo-2-propyl (meth)acrylate and 1,1-dimethyl-2-sulfoethyl (meth)acrylamide. Out of these, 2-methyl-2-(meth) acrylamidepropanesulfonic acid is preferably used. These polymerizable monomers having a sulfonate group may be used alone or in combination.

The above polymerizable monomers may be used alone or in combination as the component (A). The component (A) is preferably a polymerizable monomer having an acidic group and/or an acid anhydride group, more preferably at least one polymerizable monomer selected from carboxylic acid group, phosphoric acid group and acid anhydrides thereof. The carboxylic acid is preferably an aromatic carboxylic acid, dicarboxylic acid or adjacent dicarboxylic acid on an aromatic ring, and the phosphoric acid is preferably an alkyl ester form, particularly preferably a dialkyl ester form (R—O—PO(OH)—O—R', R and R' are alkyl groups). The component (A) is preferably a (meth)acrylic polymerizable monomer. As a matter of course, a plurality of polymerizable monomers may be used in combination. For example, a combination of a (meth)acrylic polymerizable monomer having a carboxylic acid group and/or its acid anhydride group and a (meth)acrylic polymerizable monomer having a phosphoric acid group and/or its acid anhydride group is preferred, a combination of a 4-(meth)acryloyloxyalkyltrimellitic acid-based compound and/or acid anhydride thereof and a bis{(meth)acryloyloxyalkyl}acid phosphate-based compound is more preferred, and a combination of 4-(meth)acryloyloxyethyltrimellitic acid and bis{2-(meth)acryloyloxyethyl}acid phosphate is particularly preferred because it has excellent heat stability, tooth permeability and adhesive force. High adhesion is obtained for the unground tooth by the above phosphate-based compound. The weight ratio of these monomers is preferably 10:90 to 90:10, more preferably 20:80 to 80:20, much more preferably 30:70 to 70:30.

In the dental self-etching primer composition of the present invention, the component (A) is contained in an amount of preferably 1 to 40 wt %, more preferably 3 to 35 wt %, much more preferably 4 to 30 wt %. When the amount falls below the above lower limit, adhesion degrades and when the amount exceeds the above upper limit, stability becomes worse disadvantageously.

In the dental self-etching primer composition of the present invention, the component (B) is a reducing inorganic compound containing sulfur. The compound is preferably a reducing inorganic compound containing sulfur as a redox polymerization initiator which can be used to polymerize a radically polymerizable monomer in a medium such as water.

Examples of the reducing inorganic compound include sulfurous acid, bisulfurous acid, metasulfurous acid, metabisulfurous acid, pyrosulfurous acid, thiosulfuric acid, 1-additionate, 1,2-thionic acid, hyposulfurous acid and hydrosulfurous acid and salts thereof. Out of these, sulfurous acid salts are preferred, and sodium sulfite, potassium sulfite, sodium hydrogen sulfite and potassium hydrogen sulfite are particularly preferred.

These reducing inorganic compounds may be used alone or in combination. Further, another reducing inorganic compound or reducing organic compound may be used in combination in limits that do not impair the effect of the present invention.

In the dental self-etching primer composition of the present invention, the component (B) is contained in an amount of preferably 0.1 to 10 wt %, more preferably 0.3 to 8 wt %, much more preferably 0.5 to 5 wt %. When the amount falls below the above lower limit, adhesion degrades and when the amount exceeds the above upper limit, stability becomes worse disadvantageously.

In the dental self-etching primer composition of the present invention, the component (C) is a ketone-based solvent. The ketone-based compound is not particularly limited if it is commonly used as a solvent, may be used for dental purpose without a problem and does not have marked toxicity. A ketone compound having an alkyl group is preferably used. Examples of the ketone compound include acetone, ethyl methyl ketone, diethyl ketone, methyl propyl ketone, ethyl propyl ketone and dipropyl ketone. Out of these, acetone is particularly preferred because it readily evaporates and has high compatibility with a monomer and water, and marked toxicity is not observed.

In the dental self-etching primer composition of the present invention, the component (C) is contained in an amount of preferably 5 to 50 wt %, more preferably 10 to 50 wt %, much more preferably 15 to 50 wt %. When the amount falls below the above lower limit, the composition becomes inhomogeneous and when the amount exceeds the above upper limit, the composition becomes unsatisfactory in terms of solubility disadvantageously.

In the dental self-etching primer composition of the present invention, the component (D) is water. Examples of water which can be used herein include purified water (Japanese Pharmacopoeia), distilled water, ion exchange water and physiological saline. Distilled water and ion exchange water are preferably used herein.

In the dental self-etching primer composition of the present invention, the component (D) is contained in an amount of preferably 25 to 75 wt %, more preferably 25 to 70 wt %, much more preferably 30 to 70 wt %. When the amount falls below the above lower limit, adhesion degrades and when the amount exceeds the above upper limit, the composition becomes inhomogeneous disadvantageously.

The storage stability of the dental self-etching primer composition of the present invention is 2 hours or longer at 65° C. while the above components are mixed together. The storage stability is preferably 4 hours or longer at 65° C., more preferably 8 hours or longer at 65° C. The term "storage stability" means that the composition does not gel or does not become viscous at 65° C. This storage stability is checked according to whether the composition after exposure to 65° C. develops such strength that it can stand a tensile bond strength test at not less than 15 MPa when the dentine of a bovine tooth is bonded to the Superbond (registered trademark, manufactured by Sun Medical Co., Ltd.) by using the composition as a primer in the manner prescribed. The typical bonding test method including the above prescription is as follows. That is, after the dentine of the bovine tooth is ground with water-resistant Emery paper No. 180 under pouring water and finger pressure to obtain a smooth surface, water is removed from the surface with an air gun. The primer composition to be tested is applied to the ground surface, left for 20 seconds and dried with an air gun for 3 seconds. A cement mixture of the Superbond (registered trade name, manufactured by Sun Medical Co., Ltd.) is heaped up on the primer treated surface by limiting the bonding area to a diameter of 4.8 mm, and a polyacryl cylindrical column (to be referred to as "acryl bar or acryl" hereinafter) is pressure bonded to the surface under finger pressure for 5 seconds. One hour after that, the assembly is immersed in 37° C. water for 16 hours to carry out a tensile bond strength test (cross head speed of 2 mm/min).

The dental self-etching primer composition of the present invention does not substantially contain an alcohol-based solvent. The content of the alcohol-based solvent in the composition is preferably no more than 2.5 wt %, more preferably no more than 2 wt %, much more preferably no more than 1.5 wt %. When the content exceeds the above upper limit, stability becomes worse disadvantageously. The alcohol-based solvent is a hydrocarbon having an alcoholic hydroxyl group and not preferably a lower alcohol, as exemplified by ethyl alcohol, propyl alcohol (including isomers thereof, i.e., n-propyl alcohol and isopropyl alcohol) and butyl alcohol (including isomers thereof, i.e., n-butyl alcohol, sec-butyl alcohol, isobutyl alcohol and t-butyl alcohol). Particularly ethanol is contraindicated.

The dental self-etching primer composition of the present invention may contain an organic peroxide such as benzoyl peroxide (BPO), lauryl peroxide, cumene hydroperoxide or t-butyl hydroperoxide, or inorganic peroxide such as hydrogen peroxide, ammonium persulfate, potassium persulfate, potassium chlorate, potassium bromate or potassium perphosphate; reducing organic compound such as aliphatic or aromatic secondary or tertiary amine exemplified by N,N-dimethylaminoethyl methacrylate, N,N-dimethyl-p-toluidine or N-phenylglycine; protein crosslinking agent such as aldehyde exemplified by formaldehyde or glutaraldehyde; storage stabilizer such as hydroquinone, hydroquinone monomethyl ether, hydroxymethoxybenzoquinone or butylated hydroxytoluene, polymer thickener and inorganic or organic filler in limits that do not impair the effect of the present invention, in addition to the above components (A), (B), (C) and (D).

In the present invention, a reducing organic compound component may be used in combination. Examples of the reducing organic compound include aliphatic or aromatic amines such as N,N-dimethylaniline, N,N-dimethyl-p-toluidine (DMPT), N,N-diethyl-p-toluidine, N,N-diethanol-p-toluidine, N,N-dimethyl-p-tert-butylaniline, N,N-dimethylanisidine, N,N-dimethyl-p-chloroaniline, N,N-dimethylanisidine, N,N-dimethyl-p-chloroaniline, N,N-dimethylaminobenzoic acid and alkyl esters thereof, N,N-diethylaminobenzoic acid and alkyl esters thereof, N,N-dimethylaminobenzaldehyde, N,N-diethylaminobenzaldehyde, N,N-dimethylaminoethyl(meth)acrylate and N,N-diethylaminoethyl(meth)acrylate; aromatic sulfinic acid and salts thereof (Li, Na, K, Mg and Ca salts) such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid; amine compounds represented by the following formula (I) such as N-phenylglycine (NPG), N-tolylglycine and N,N-(3-methacryloyloxy-2-hydroxypropyl)phenylglycine; and reducing sugars such as ascorbic acid and derivatives thereof.

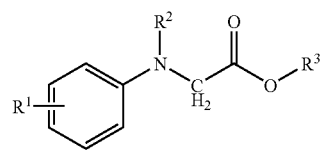

(I)

(wherein $R^1$ and $R^2$ are each independently a hydrogen atom or alkyl group which may have a functional group or substituent, and $R^3$ is a hydrogen atom or metal).

These reducing organic compounds may be used alone or in combination. A combination including NPG is particularly preferred.

Out of these reducing organic compounds, (E) a reducing organic compound component containing sulfur is preferred, sulfinic acid is more preferred, p-toluenesulfinic acid is much more preferred, and sodium p-toluenesulfinate is particularly preferred.

The dental self-etching primer kit of the present invention comprises the above dental self-etching primer composition of the present invention. This kit is composed of a composition I containing the above component (A) and/or the above component (B) and a composition II different from the composition I. In the kit containing the above component (E), the component (E) is preferably contained in the composition II separate from the composition I which contains the component (A) and/or the component (B). Thereby storage stability is improved.

The solvent for the above composition II is not particularly limited but preferably water and/or an alcohol. Preferred examples of the alcohol include ethyl alcohol, propyl alcohol (including isomers thereof, i.e., n-propyl alcohol and isopropyl alcohol), butyl alcohol (including isomers thereof, i.e., n-butyl alcohol, sec-butyl alcohol, isobutyl alcohol and t-butyl alcohol) and mixtures thereof. Out of these, ethyl alcohol is preferred.

As for the composition of the composition II, the content of the reducing organic compound component containing sulfur (E) is preferably 0.2 to 20 wt %, more preferably 0.5 to 10 wt %, much more preferably 1 to 5 wt %. The content of water is preferably 15 to 85 wt %, more preferably 33 to 65 wt %, much more preferably 43 to 54 wt %, and the content of the alcohol is preferably 15 to 85 wt %, more preferably 33 to 65 wt %, much more preferably 43 to 54 wt %. The total content of these components should not exceed 100 wt %.

Since the dental self-etching primer kit contains the above composition II, it has the ability of recovering a reduction in adhesive force caused by oxidative sterilization with a hypochlorite.

As for the application method, after the tooth is treated with the composition II, the composition I may be applied or vice versa, or right before application, the both compositions may be mixed together.

More specifically, after the tooth is sterilized with NaOCl or the like, rinsed in water and preferably further dried with air, it is treated with the above compositions I and II, left to stand for 10 to 60 seconds, and then the adhesive is applied to the tooth.

EXAMPLES

The following examples are provided for the purpose of further illustrating the present invention but are in no way to be taken as limiting.

Examples 1 to 5

A tooth sample prepared by removing a fresh front tooth from a bovine mandible and preserving it by freezing in water was used. The unfrozen bovine tooth was ground with water-resistant Emery paper No. 180 by the ECOMET-III rotary grinding machine (of BUEHLER Ltd.) under pouring water and finger pressure to obtain smooth enamel and dentine surfaces, and water was removed from these surfaces with an air gun. The dental self-etching primer compositions of the present invention having composition shown in Table 1 were applied to the ground surfaces, left for 20 seconds and dried with an air gun for 3 seconds. 0.15 mm-thick specified paper having a round hole with a diameter of 4.8 mm was placed and fixed on this coating film to specify a bonding area. The hole was filled with the Superbond (registered trade name, manufactured by Sun Medical Co., Ltd.) as a curable resin composition in the manner prescribed, and an acryl bar was bonded to the ground surfaces and left for 15 minutes to prepare specimens.

After these specimens were immersed in 37° C. water for 16 hours or a 55° C. hot water bath and a 5° C. cold water bath alternately 5,000 times (TC=5,000 times), a tensile bond strength test (cross head speed of 2 mm/min) was conducted.

The results are shown in Table 1.

TABLE 1

| | Composition (wt %) | | | | | Adhesion strength (MPa) | | | |
| | | | | | | Dentine | | Enamel | |
| | [A] | [C] | [D] Purified | [B] | | 37° C. · 16 hr | TC 5000 times | 37° C. · 16 hr | TC 5000 times |
| | 4MET | P2M | Acetone | water | Na$_2$SO$_3$ | | | | |
| Example 1 | 0 | 20 | 30 | 47.5 | 2.5 | 24.3 ± 3.4 | 16.4 ± 1.3 | 14.8 ± 4.1 | 14.6 ± 2.9 |
| Example 2 | 5 | 15 | 30 | 47.5 | 2.5 | 22.6 ± 1.2 | 15.7 ± 2.1 | 14.8 ± 1.3 | 10.0 ± 4.3 |
| Example 3 | 10 | 10 | 30 | 47.5 | 2.5 | 18.0 ± 4.1 | 20.6 ± 4.6 | 14.2 ± 5.4 | 11.9 ± 2.4 |
| Example 4 | 15 | 5 | 30 | 47.5 | 2.5 | 19.3 ± 3.7 | 16.6 ± 2.4 | 12.6 ± 2.1 | 16.0 ± 4.2 |
| Example 5 | 20 | 0 | 30 | 47.5 | 2.5 | 17.1 ± 1.6 | 17.0 ± 0.7 | 18.7 ± 2.6 | 15.2 ± 0.8 |

The abbreviations in Table 1 and tables below denote the following substances.
P2M: bis(methacryloyloxyethyl)acid phosphate
4MET: 4-methacryloyloxyethyltrimellitic acid
NPG•Na: sodium N-phenylglycine
p-TSNa: sodium p-toluenesulfinate
EtOH: ethanol Examples 6 to 9

After specimens were produced in the same manner as in Examples 1 to 5 by using compositions shown in Table 2 and immersed in 37° C. water for 16 hours, a tensile bond strength test was carried out on these specimens. The results shown in Table 2 were obtained.

TABLE 2

| | Composition (wt %) | | | | | Adhesion strength(MPa) (after 16 hours of heating 37° C.) | |
|---|---|---|---|---|---|---|---|
| | [A] | | [C] Ace-tone | [D] Purified water | [B] Na$_2$SO$_3$ | Dentine | Enamel |
| | P2M | 4MET | | | | | |
| Ex. 6 | 10 | — | 30 | 59.5 | 0.5 | 21.1 ± 6.1 | 11.7 ± 0.4 |
| Ex. 7 | — | 10 | 30 | 57.5 | 2.5 | 16.8 ± 0.2 | 12.9 ± 1.3 |
| Ex. 8 | — | 30 | 30 | 37.5 | 2.5 | 18.4 ± 2.0 | 15.6 ± 2.8 |
| Ex. 9 | 10 | 10 | 30 | 49.5 | 0.5 | 19.7 ± 3.7 | 13.5 ± 3.1 |

Ex.: Example

Comparative Examples 1 to 3

After specimens were produced in the same manner as in Examples 1 to 5 by using compositions shown in Table 3 in which the component (B) differed from that of the present invention and immersed in 37° C. water for 16 hours, a tensile bond strength test was carried out on these specimens. The results shown in Table 3 were obtained.

TABLE 3

| | Composition (wt %) | | | | | Adhesion strength (MPa) (after 16 hours of heating 37° C.) | |
|---|---|---|---|---|---|---|---|
| | [A] | [C] Ace-tone | [D] Puri-fied water | [B] NPG·Na | p-TSNa | Dentine | Enamel |
| | 4MET | | | | | | |
| C. Ex. 1 | 30 | 30 | 40 | — | — | 1.7 ± 0.2 | 10.5 ± 2.3 |
| C. Ex. 2 | 30 | 30 | 37.5 | 2.5 | — | 3.0 ± 2.2 | |
| C. Ex. 3 | 30 | 30 | 37.5 | — | 2.5 | 2.8 ± 0.8 | |

C. Ex.: Comparative Example

Examples 10 to 12

After a storage stability test was conducted on primer compositions having the same composition as in Example 3 at a heating temperature shown in Table 4 for a heating time shown in Table 4, specimens were produced in the same manner as in Example 1 to 5 by using the same composition as in Example 3 and immersed in 37° C. water for 16 hours. When a tensile bond strength test was carried out on these specimens, the results shown in Table 4 were obtained.

TABLE 4

| | Ex. 10 | | Ex. 11 | | Ex. 12 | |
|---|---|---|---|---|---|---|
| Heating temperature (° C.) | 55 | | 65 | | 75 | |
| Heating time (hr) | 188 | 233 | 18 | 24 | 2 | 3 |
| Stability | ○ | X | ○ | X | ○ | X |
| adhesion strength: dentine | 22.1 ± 2.8 | — | 18.6 ± 0.9 | — | 17.0 ± 4.6 | — |

TABLE 4-continued

| | Ex. 10 | Ex. 11 | Ex. 12 |
|---|---|---|---|
| (after 16 hours of heating 37° C.) | | | |

The criteria for the evaluation of stability are given below.
○: specimen does not change in appearance
Δ: specimen becomes viscous
X: specimen gels

Comparative Examples 4 to 6

After primer compositions having compositions shown in Table 5 were prepared and left at room temperature for 16 hours, their stabilities were evaluated based on the above criteria. The results shown in Table 5 were obtained.

TABLE 5

| | Composition (wt %) | | | | | |
|---|---|---|---|---|---|---|
| | [A] | | [C] | [D] Purified | [B] | Stability |
| | 4MET | P2M | EtOH | water | Na$_2$SO$_3$ | |
| C. Ex. 4 | 0 | 20 | 30 | 47.5 | 2.5 | X |
| C. Ex. 5 | 20 | 0 | 30 | 47.5 | 2.5 | Δ |
| C. Ex. 6 | 10 | 10 | 30 | 47.5 | 2.5 | X |

C. Ex.: Comparative Example

Examples 13 to 16

After a storage stability test was conducted on primer compositions having the same composition as in Example 3 at a heating temperature shown in Table 6 for a heating time shown in Table 6, specimens were produced by carrying out the following treatments (1) to (4) on the same composition as in Example 3 and immersed in 37° C. water for 16 hours. The results shown in Table 6 were obtained.

Treatment 1

A tooth sample prepared by removing a fresh front tooth from a bovine mandible and preserving it by freezing in water was used. The unfrozen bovine tooth was ground with water-resistant Emery paper No. 180 by the ECOMET-III rotary grinding machine (of BUEHLER Ltd.) under pouring water and finger pressure to obtain a smooth dentine surface. Water was removed from the ground bovine tooth with an air gun. The primer composition was applied to the ground surface, left for 20 seconds and dried with an air gun for 3 seconds. 0.15 mm-thick paper having a round hole with a diameter of 4.8 mm was placed and fixed on this coating film to specify a bonding area. The hole was filled with the D Liner Dual (registered trade name) (to be abbreviated as "DLD" hereinafter) of Sun Medical Co., Ltd. as a curable resin composition in the manner prescribed, left for 20 seconds, dried with an air gun for 3 seconds and exposed to light for 10 seconds. After the Metafil C (registered trade name, manufactured by Sun Medical Co., Ltd.) as a composite resin was cured in the manner prescribed, the Superbond cement mixture was heaped up on an acryl bar, and the acryl bar was pressure contacted to the surface of the Metafil C cured product and left for 15 seconds to produce test specimens.

After these specimens were immersed in 37° C. water for 16 hours, a tensile bond strength test (cross head speed of 2 mm/min) was conducted.

Treatment 2

The above treatment 1 was repeated except that the D Liner Dual was coated, left for 60 seconds and not exposed to light.

Treatment 3

The above treatment 2 was repeated except that the hole was filled with amalgam in place of the Metafil C.

Treatment 4: Micro Tensile Bond Strength Test

A columnar cavity having a diameter of 4 mm was formed in the root portion of a bovine tooth which was unfrozen right before the test to enlarge a root canal. After water in the enlarged root canal was removed with an air gun, the primer composition was applied to the root canal, left for 20 seconds and dried with an air gun for 3 seconds.

Then, the Superbond root filling sealer (registered trade name, manufactured by Sun Medical Co., Ltd.) was filled into the root canal and cured in the manner prescribed to prepare a specimen.

The specimen was left in a thermostat tank kept at a relative humidity of 95% and a temperature of 37° C. for 24 hours and cut into half on a plane passing through the center of the columnar cavity filled with the composition in parallel to the direction of the root canal. A 10 $mm^3$ acryl cube was bonded to the divided surface by the Superbond C & B (manufactured by Sun Medical Co., Ltd.) and cut to a thickness of about 1 mm in a direction perpendicular to the direction of the root canal with the ISOMET low-speed rotary diamond cutter (of BUEHLER Ltd.) after the passage of 20 minutes. Further, the obtained piece was trimmed into a dumbbell form (thinnest portion: interface between the tooth and the filled composition) to ensure that the bonded area became 1 $mm^2$ and then, a micro tensile bond strength (MTBS) test was conducted with the EZ-TEST small-sized desk-top tester (of Shimadzu Corporation) at a cross head speed of 1 mm/min.

Treatment 10-3

As Reference Examples of the above treatments 1 to 4, treatment 10-3 (application of an aqueous solution containing 10% of citric acid and 3% of ferric chloride) was carried out in place of the pre-treatment with the primer of the present invention. The results shown in Table 6 were obtained.

TABLE 6

| Example | Treatment | Pre-treatment material | Adhesion strength (MPa) (after 16 hours of heating 37° C.) | Measurement method |
|---|---|---|---|---|
| R. Ex. 1 | (1) | 10-3 | 11.0 ± 1.7 (30 · 10 · 10) | Ordinary Tensile test |
| Ex. 13 | | Primer | 19.3 ± 3.9 (acryl · tooth · 100) | |
| R. Ex. 2 | (2) | 10-3 | 10.1 ± 2.8 (60 · 60 · 30) | |
| Ex. 14 | | Primer | 20.3 ± 2.6 (tooth · tooth · 100) | |
| R. Ex. 3 | (3) | 10-3 | 3.3 ± 2.0 (DLD/amalgam) | |
| Ex. 15 | | Primer | 2.2 ± 0.9 (DLD/amalgam) | |
| R. Ex. 4 | (4) | 10-3 | 38.8 ± 8.3 (mixed destruction) | MTBS |
| Ex. 16 | | Primer | 36.5 ± 4.8 (mixed destruction) | |

R. Ex.: Reference Example
Ex.: Example (($n^1.n^2.n^3$) within the parentheses in the lower part of the column for adhesion strength in the table indicate the result of the first test, the result of the second test and the result of the third test, respectively. When a raw material is given in that part, it shows the result of the test in which destruction occurred with the raw material, when "raw material A/raw material B" is given, it means that peeling occurred between the raw material A and the raw material B, and when a numeral is given, it signifies the area percentage of the resin remaining on the tooth surface on the destruction section.)

Examples 17 and 18 and Comparative Examples 7 to 9

When a heat stability test was conducted on compositions containing ethanol in an amount shown in Table 7, the results shown in Table 7 were obtained.

TABLE 7

| | 4MET/P2M/Aceton/EtOH/ Purified water/$Na_2SO_3$ | Stability (room temperature) One night | 65° C. heating acceleration 2 hr | 24 hr |
|---|---|---|---|---|
| Example 17 | 10/10/30/0/47.5/2.5 | ○ | ○ | ○ |
| Example 18 | 10/10/27.5/2.5/47.5/2.5 | ○ | ○ | x |
| Comparative Example 7 | 10/10/25/5/47.5/2.5 | ○ | x | x |
| Comparative Example 8 | 10/10/1/29/47.5/2.5 | ○ | x | x |
| Comparative Example 9 | 10/10/0.5/29.5/47.5/2.5 | x | x | x |

Stability and 65° C. heating acceleration were evaluated based on the following criteria.
○: composition does not change in appearance
Δ: composition becomes viscous
x: composition gels Examples 19 to 21 and Comparative Example 10

Specimens were produced in the same manner as in Examples 1 to 5 except that the following sterilization was carried out in place of the removal of water with an air gun before an etching primer treatment and the following etching primer prescription was carried out, and immersed in 37° C. water for 16 hours to carry out a tensile bond strength test. The results shown in Table 8 were obtained.

(Sterilization)

A canal cleaner (manufactured by Fukuchi Pharmaceutical Co., Ltd., containing 10 wt % of sodium hypochlorite) was applied and left for 60 seconds.

Etching Primer Prescription (A)

The above coating film was cleaned with water/air by using a three-way syringe (manufactured by J. MORITA MFG. CORP.) for 10 seconds, a composition i having the following composition was applied to the treated surface and left for 20 seconds, and a composition ii having the following composition was applied to the coating film and left for 10 seconds.

Etching Primer Prescription (B)

The obtained coating film was cleaned with water/air by using a three-way syringe for 10 seconds, one drop of the composition i and one drop of the composition ii were mixed together, and the resulting mixture was instantly applied to the treated surface and left for 20 seconds.

Etching Primer Prescription (B')

The etching primer prescription (B) was repeated except that cleaning with water/air was changed to cleaning only with air and the standing time after the application of the etching primer was changed from 10 seconds to 60 seconds.

Etching Primer Prescription (C)

The obtained coating film was cleaned with water/air by using a three-way syringe for 10 seconds, a surface treatment material Green was applied to the treated surface and left for 10 seconds, and the composition ii was applied and left for 10 seconds. The above compositions have the following compositions.

(Composition i)
4-MET: 10 wt %
P-2M: 10 wt %
Acetone: 30 wt %
Purified water: 47.5 wt %
$Na_2SO_3$: 2.5 wt %
4-methoxyphenol: 0.03 wt %
(Composition ii)
sodium p-toluenesulfinate: 3 wt %
ethanol: 48.5 wt %
purified water: 48.5 wt %
(Green)
citric acid: 10 wt %
ferric chloride: 3 wt %
purified water: 87 wt %
blue No. 1: trace amount

TABLE 8

| | Etching primer prescription | Adhesive force (MPa) (after 16 hours of heating at 37° C.) |
|---|---|---|
| Example 19 | (A) | 19 ± 2.7 |
| Example 20 | (B) | 19.1 ± 1.3 |
| Example 21 | (B') | 9.7 ± 1.1 |
| Comparative Example 10 | (C) | 12.6 ± 3.1 |

Example 22 and Comparative Example 11

The procedure of Example 1 was repeated except that only dental cuticles and deposits were removed from a bovine tooth by polishing with a neopolishing cream and an electric hand piece in place of grinding, the tooth was rinsed in water and the etching primer prescription was changed as shown in Table 9. The results shown in Table 9 were obtained.

TABLE 9

| | Etching primer prescription | Adhesive force of enamel (MPa) (5,000 times of TC) |
|---|---|---|
| Example 22 | (D) | 25.5 ± 5.6 |
| Comparative Example 11 | (E) | 12.6 ± 3.1 |

Etching Primer Prescription (D)
After water was removed with an air gun, the composition was applied, left for 5 seconds and dried with air.
Etching Primer Prescription (E)
After water was removed with an air gun, Red was applied, left for 30 seconds, rinsed in water and dried with air.
(Red)
phosphoric acid: 69 wt %
purified water: 28 wt %
PVA: 3 wt %
Yellow No. 5 and ethyl vanilline: trace amounts

The invention claimed is:
1. A dental self-etching primer composition comprising a mixture of
   (A) a polymerizable monomer having one polymerizable group, which polymerizable group is a polymerizable monomer having an acidic group and/or an acid anhydride group, and which polymerizable monomer comprises at least one phosphoric acid group and/or an acid anhydride thereof,
   (B) a reducing inorganic compound selected from at least one of the group consisting of sulfurous acid, bisulfurous acid, and salts thereof,
   (C) a ketone-based solvent,
   (D) water, and optionally
   (E) an alcohol-based solvent in an amount of no more than 2.5 weight-% based on the weight of the composition, said composition having a storage stability of 2 hours or longer at 65° C.

2. The dental self-etching primer composition according to claim 1, wherein the content of the alcohol-based solvent is no more than 1.5 wt %.

3. The dental self-etching primer composition according to claim 1, wherein the alcohol-based solvent is ethanol.

4. The dental self-etching primer composition according to claim 1, wherein the component (A) includes a polymerizable monomer having at least one carboxylic acid group and/or an acid anhydride thereof and a polymerizable monomer having at least one phosphoric acid group and/or an acid anhydrides thereof in the weight ratio of 10:90 to 90:10.

5. The dental self-etching primer composition according to claim 1, wherein the component (A), other than the polymerizable monomer having at least one phosphoric acid group and/or acid anhydrides thereof, is a (meth)acrylic polymerizable monomer.

6. The dental self-etching primer composition according to claim 1, wherein the component (A), other than the polymerizable monomer having at least one phosphoric acid group and/or acid anhydrides thereof, is at least one polymerizable monomer selected from the group consisting of 4-(meth)acryloyloxyalkyltrimellitic acid and acid anhydrides thereof.

7. The dental self-etching primer composition according to claim 1, wherein the component (B) is sulfurous acid and/or a salt thereof.

8. The dental self-etching primer composition according to claim 1, wherein the component (C) is acetone.

9. The dental self-etching primer composition according to claim 1, which comprises 1 to 40 wt % of the component (A), 0.1 to 10 wt % of the component (B), 5 to 50 wt % of the component (C) and 25 to 75 wt % of the component (D), and has a storage stability of 2 hours or longer at 65° C. which is useful for a long-term storage.

10. The dental self-etching primer composition according to claim 1, which further comprises (E) a reducing organic compound containing sulfur.

11. The dental self-etching primer composition according to claim 10, wherein the component (E) is a sulfinic acid-based compound.

12. A dental self-etching primer kit comprising the dental self-etching primer composition of claim 1, wherein the kit is composed of a composition I and a composition II, and the component (E) is contained in the composition II separate from the composition I containing the component (A) and/or the component (B).

13. The dental self-etching primer kit according to claim 12, wherein the composition II contains at least the component (E) and an alcohol-based solvent.

14. The dental self-etching primer kit according to claim 12, which has the ability of recovering a reduction in adhesive force caused by an oxidizer treatment.

15. The dental self-etching primer composition according to claim 1, wherein the components (C) and (D) are in amounts of 5 to 50 wt % and 25 to 75 wt %, respectively.

* * * * *